(12) United States Patent
Yu et al.

(10) Patent No.: US 11,510,627 B2
(45) Date of Patent: Nov. 29, 2022

(54) CARDIAC CATHETER CONTACT FORCE DETERMINATION

(71) Applicant: APN Health, LLC, Pewaukee, WI (US)

(72) Inventors: Xuyong Yu, Oak Creek, WI (US); Stephen J. Merrill, Racine, WI (US); Jasbir Sra, Oak Creek, WI (US)

(73) Assignee: APN Health, LLC, Pewaukee, WI (US)

( * ) Notice: Subject to any disclaimer, the term of this patent is extended or adjusted under 35 U.S.C. 154(b) by 507 days.

(21) Appl. No.: 16/743,432

(22) Filed: Jan. 15, 2020

(65) Prior Publication Data

US 2020/0222006 A1 Jul. 16, 2020

Related U.S. Application Data

(60) Provisional application No. 62/918,049, filed on Jan. 15, 2019.

(51) Int. Cl.
*A61B 5/00* (2006.01)
*A61B 6/00* (2006.01)
(Continued)

(52) U.S. Cl.
CPC .......... *A61B 5/6852* (2013.01); *A61B 5/0536* (2013.01); *A61B 5/352* (2021.01);
(Continued)

(58) Field of Classification Search
CPC ....... A61B 5/352; A61B 6/503; A61B 5/6852; A61B 5/7264; A61B 5/6885; A61B 5/063;
(Continued)

(56) References Cited

U.S. PATENT DOCUMENTS 5,743,903 A 4/1998 Stern et al.
5,938,660 A 8/1999 Swartz et al.
(Continued)

FOREIGN PATENT DOCUMENTS

AU 2018/220134 3/2019
WO 2010/078453 A1 7/2010
(Continued)

OTHER PUBLICATIONS

"Role of Contact Force Sensing in Catheter Ablation of Cardiac Arrhythmias" by Ariyarathna et al., Journal of the American College of Cardiology: Clinical Electrophysiology, vol. 4, Issue 6, pp. 707-723, Jun. 2018.
(Continued)

*Primary Examiner* — Mark D Remaly
(74) *Attorney, Agent, or Firm* — Jansson Munger McKinley & Kirby Ltd.

(57) ABSTRACT

An automatic method of categorizing the contact force of a catheter tip against a portion of a patient's heart based on motion of the catheter tip, the method comprising (a) capturing a series of 3D-coordinate data points of the catheter tip as a function of discrete times with a 3D medical imaging system, the 3D coordinates corresponding to an orthogonal 3-axis spatial coordinate system, (b) using a programmable computing system, computing a set of measures based on the series of 3D-coordinate data points, (c) categorizing each measure by a respective set of predetermined threshold values; and (d) combining the categorized measures to yield a relative quality of the contact force.

15 Claims, 15 Drawing Sheets

(51) Int. Cl.
*A61B 5/0536* (2021.01)
*A61B 5/352* (2021.01)

(52) U.S. Cl.
CPC .......... *A61B 5/7264* (2013.01); *A61B 6/485* (2013.01); *A61B 6/503* (2013.01); *A61B 6/5205* (2013.01)

(58) Field of Classification Search
CPC ......... A61B 5/0536; A61B 6/485; A61B 6/12; A61B 6/487; A61B 6/5205
See application file for complete search history.

(56) References Cited

U.S. PATENT DOCUMENTS

| | | | |
|---|---|---|---|
| 8,206,380 B2 | 6/2012 | Lenihan et al. | |
| 8,357,152 B2 | 1/2013 | Govari et al. | |
| 8,369,922 B2 | 2/2013 | Paul et al. | |
| 8,460,285 B2 | 6/2013 | Wang et al. | |
| 8,668,686 B2 | 3/2014 | Govari et al. | |
| 8,728,077 B2 | 5/2014 | Paul et al. | |
| 8,755,860 B2 | 6/2014 | Paul et al. | |
| 9,149,327 B2 | 10/2015 | Lambert et al. | |
| 10,492,846 B2 | 12/2019 | Lambert et al. | |
| 2004/0127894 A1* | 7/2004 | Eick | A61B 34/20 606/41 |
| 2007/0100332 A1 | 5/2007 | Paul et al. | |
| 2007/0123764 A1 | 5/2007 | Thao et al. | |
| 2008/0015568 A1 | 1/2008 | Paul et al. | |
| 2008/0161796 A1 | 7/2008 | Cao et al. | |
| 2008/0249522 A1 | 10/2008 | Pappone et al. | |
| 2008/0275428 A1 | 11/2008 | Tegg et al. | |
| 2008/0275465 A1 | 11/2008 | Paul et al. | |
| 2008/0288038 A1 | 11/2008 | Paul et al. | |
| 2009/0076476 A1 | 3/2009 | Barbagli et al. | |
| 2009/0312754 A1 | 12/2009 | Lenihan et al. | |
| 2010/0168620 A1 | 7/2010 | Klimovitch et al. | |
| 2011/0022045 A1 | 1/2011 | Cao et al. | |
| 2012/0209260 A1 | 8/2012 | Lambert et al. | |
| 2013/0190726 A1 | 7/2013 | Kesner et al. | |
| 2016/0106957 A1 | 4/2016 | Olson et al. | |
| 2017/0127974 A1 | 5/2017 | Bonyak et al. | |
| 2017/0143416 A1 | 5/2017 | Guler et al. | |
| 2017/0290617 A1 | 10/2017 | Rankin et al. | |
| 2017/0319279 A1 | 11/2017 | Fish et al. | |
| 2017/0354467 A1 | 12/2017 | Rankin et al. | |
| 2018/0280081 A1 | 10/2018 | Olson et al. | |
| 2019/0038227 A1 | 2/2019 | Gelman et al. | |
| 2019/0340837 A1 | 11/2019 | Shmayahu et al. | |

FOREIGN PATENT DOCUMENTS

| | | | |
|---|---|---|---|
| WO | 2016/181315 A1 | 11/2016 | |
| WO | WO-2016181316 A1 * | 11/2016 | ......... A61B 18/1492 |
| WO | 2018/092059 A1 | 5/2018 | |

OTHER PUBLICATIONS

TactiCath™ Quartz Contact Force Ablation Catheter by St. Jude Medical. <https://www.cardiovascular.abbott/us/en/hcp/products/electrophysiology/ablation-technology/tacticath-se-ablation-catheter/about/product-features.html>.

"Catheter-Tissue Contact Force Determines Atrial Electrogram Characteristics Before and Lesion Efficacy After Antral Pulmonary Vein Isolation in Humans" by Kumar et al., Journal of Cardiovascular Electrophysiology, vol. 25, Issue 2, pp. 122-129, Feb. 2014.

PCT International Application No. PCT/US2020/13659. International Search Report and Written Opinion dated Apr. 24, 2020 (14 pages).

* cited by examiner

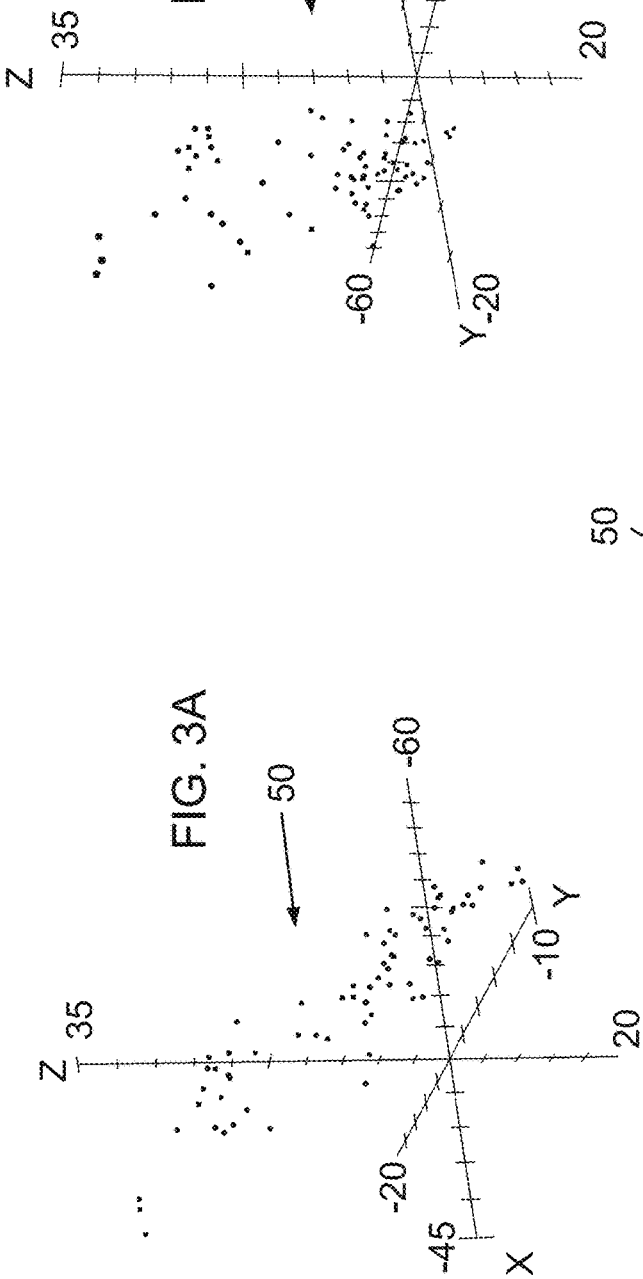
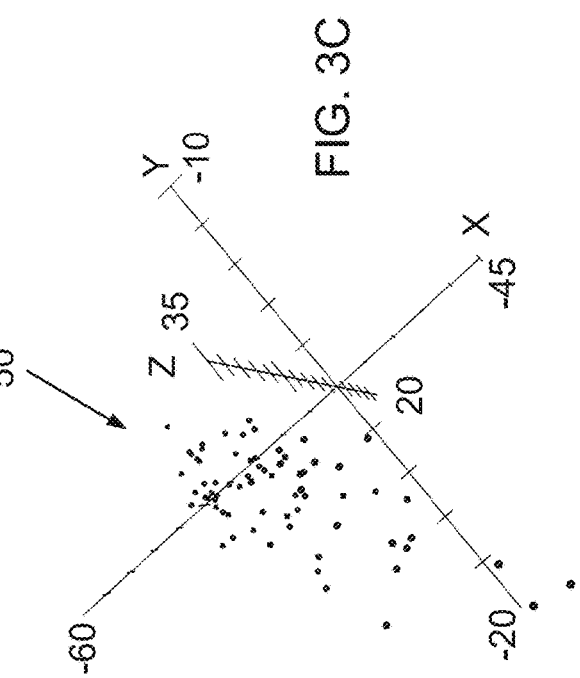

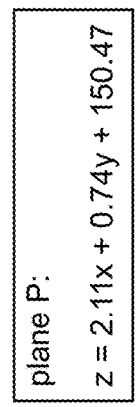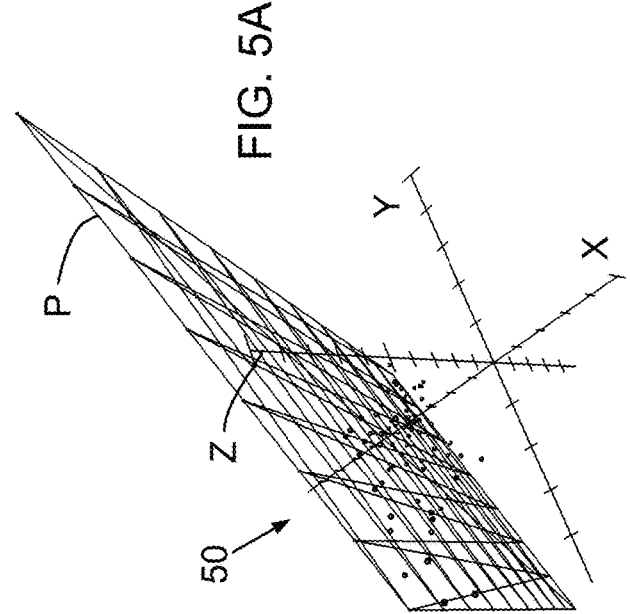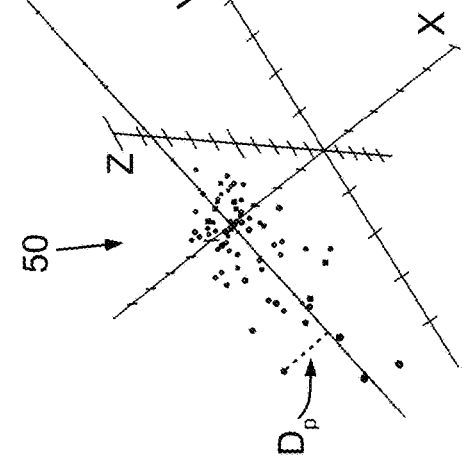

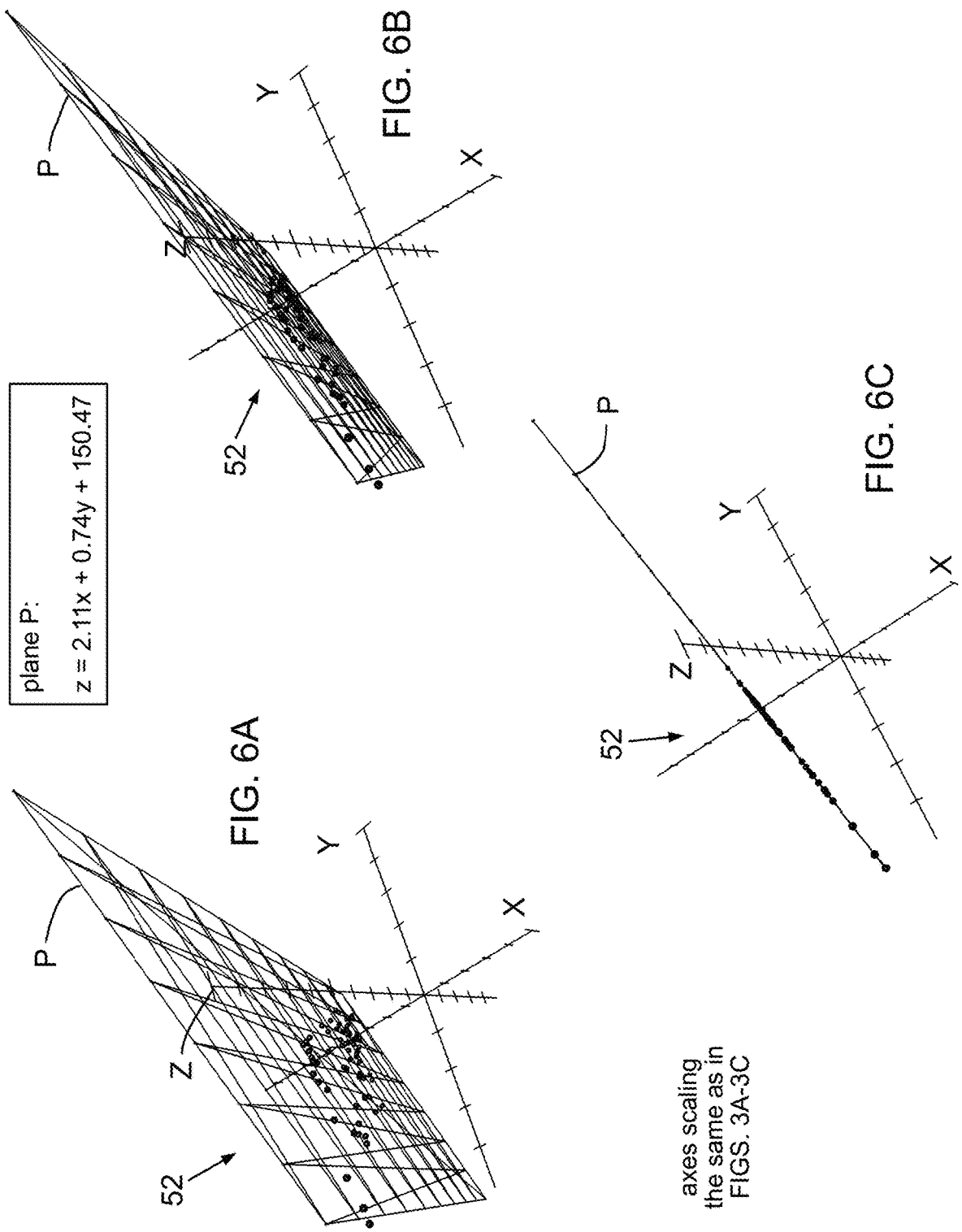

$m_3 = 0.69$ mm$^2$

| data set | $cm_1$ | $cm_2$ | $cm_3$ | $q_{CF}$ |
|---|---|---|---|---|
| 1 | medium | big | dissimilar | good |
| 2 | big | medium | similar | good |
| 3 | small | medium | dissimilar | good |
| 4 | big | small | dissimilar | weak |
| 5 | medium | medium | similar | good |
| 6 | small | medium | similar | good |
| 7 | small | medium | similar | good |
| 8 | medium | big | dissimilar | good |
| 9 | big | medium | dissimilar | medium |
| 10 | medium | medium | dissimilar | medium |
| 11 | small | medium | dissimilar | good |
| 12 | small | big | dissimilar | good |
| 13 | small | big | dissimilar | good |
| 14 | small | medium | similar | good |
| 15 | small | small | dissimilar | medium |
| 16 | medium | medium | dissimilar | weak |
| 17 | small | big | similar | strong |

FIG. 10

| $cm_1$ | $cm_2$ | $cm_3$ | $q_{CF}$ |
|---|---|---|---|
| small | big | similar | strong |
| medium | big | similar | good |
| medium | small | dissimilar | medium |
| big | medium | dissimilar | weak |

FIG. 11

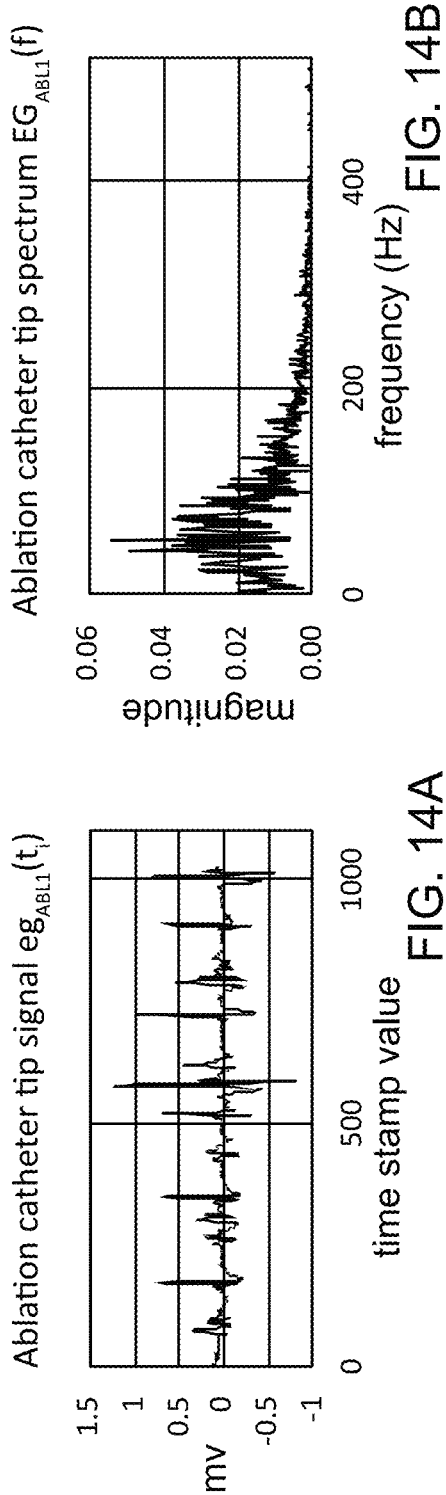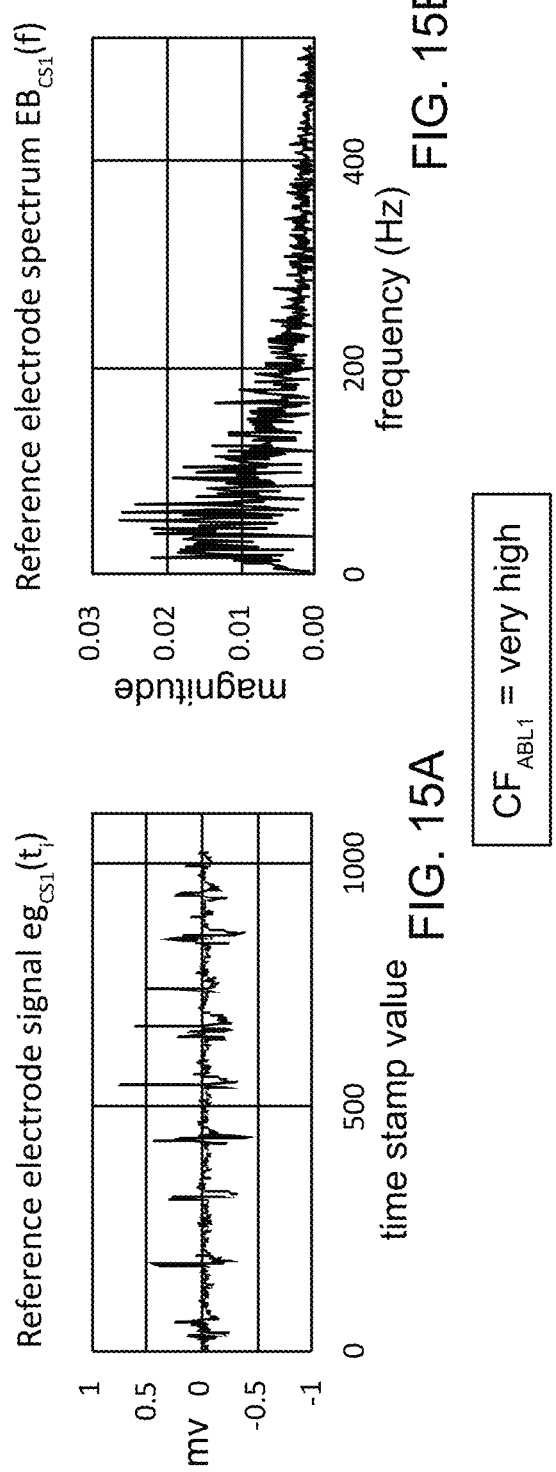
FIG. 14A FIG. 14B FIG. 15A FIG. 15B

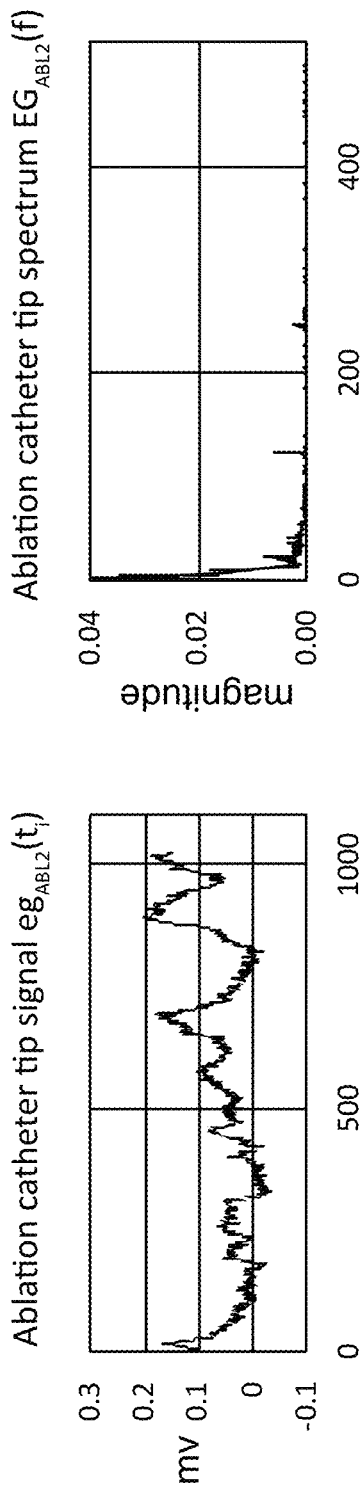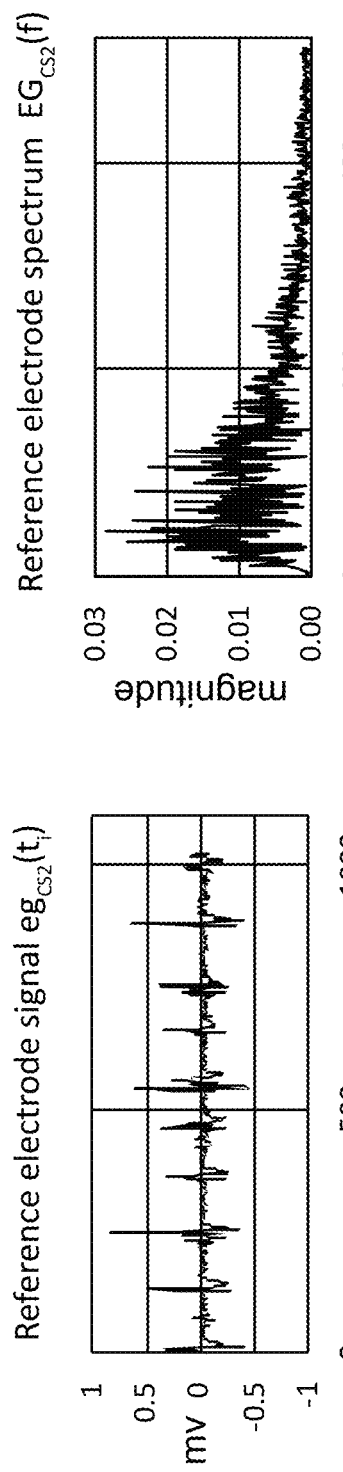
FIG. 17A  FIG. 17B  FIG. 18A  FIG. 18B
$CF_{ABL2}$ = very low

CARDIAC CATHETER CONTACT FORCE DETERMINATION

RELATED APPLICATIONS

This application claims the benefit of U.S. Provisional Application 62/918,049, filed on Jan. 15, 2019, the entire contents of which is incorporated herein by reference.

FIELD OF THE INVENTION

The present invention generally relates to the field of cardiology and more particularly to certain interventional cardiac procedures which require the navigation and manipulation of catheters.

BACKGROUND OF THE INVENTION

The force with which a cardiac catheter tip contacts various structures in a patient's heart is an important indication of how well an electrical signal may be captured by an electrode on the catheter and how effectively an interventional procedure such as cardiac ablation can be carried out.

An informative state-of-the-art review paper published in the Journal of the American College of Cardiology: Clinical Electrophysiology, Volume 4, Issue 6, June 2018 is titled "Role of Contact Force Sensing in Catheter Ablation of Cardiac Arrhythmias: Evolution or History Repeating Itself?" by Nilshan Ariyarathna et al. and is available on the Internet at http://electrophysiology.onlinejacc.org/content/4/6/707.

Contact force is broadly used as a predictor for catheter ablation efficacy as well as an important factor with respect to ablation safety during an ablation procedure. There is a strong correlation between electrode/tissue contact force and the resulting lesion volume. If the electrode/tissue contact force is too weak, there is no guarantee that a lesion of the proper size will form to destroy the desired region of tissue. Conversely, contact force which is too strong may result in complications such as perforation or tamponade. Cardiac tamponade is compression of the heart caused by an accumulation of fluid in the pericardial sac. Both perforation and tamponade are extremely serious and life-threatening events.

For these and other reasons, there is a need for the cardiologist to know something about the catheter contact force levels during interventional medical procedures. Currently there exist a number of approaches to measuring and/or estimating catheter-tip contact force. Many of these approaches are referred to in U.S. Pat. No. 10,492,846 ("Prediction of Atrial Wall Electrical Reconnection Based on Contact Force Measured During RF Ablation") assigned to St. Jude Medical International Holding S.a r.l. in Luxembourg. Among the approaches for measuring catheter-tip contact force mentioned in this document are force sensors employing ultrasound, magnetic, impedance, strain gauge, piezoelectric, and fiber optic strain measurement.

St. Jude Medical markets a product, the TactiCath™ Quartz Contact Force Ablation Catheter, which uses a fiber optic interrogator employing a Fabry-Perot interferometer cavity to measure strain (displacement) within a titanium sensor.

There are also indirect approaches to determinating catheter-tip contact force, such as impedance measurement, electrogram signal quality, and thermal approaches. U.S. Pat. No. 8,206,380 ("Method and Apparatus for Measuring Catheter Contact Force During a Medical Procedure") assigned to Advanced Cardiac Therapeutics Inc. of Long Beach, Calif., discloses an indirect method for measuring the contact force exerted on tissue. A probe heats the tissue, and the output of a radiometer indicates the temperature at depth of the tissue contacted by the probe.

U.S. Pat. No. 8,755,860 ("Method for Displaying Catheter Electrode-tissue Contact in Electro-anatomic Mapping and Navigation System") assigned to St. Jude Medical Atrial Fibrillation Division, Inc. of St. Paul, Minn., discloses another indirect approach to contact force determination based on the electrical properties of cardiac tissue by measuring the electrode/tissue coupling of an alternating current electrical signal.

The characteristics of a cardiac electrogram are another indirect source of information for cardiac catheter contact force during a cardiac ablation procedure just prior to the ablation process itself, and also reveal useful information during the ablation process. Kumar et al, in a paper titled "Catheter-Tissue Contact Force Determines Atrial Electrogram Characteristics Before and Lesion Efficacy After Antral Pulmonary Vien Isolation in Humans" in the *Journal of Electrophysiology*, 25.2 (2014), pp. 122-129, reported on a study to evaluate cardiac catheter contact force using signal features such as the electrogram amplitude. However, the correlation between the contact force and the features extracted from the electrogram was not an effective measure of contact force. Since the level of contact force does have an effect on the degree of the electrical coupling between a cardiac electrode and cardiac tissue, there remains opportunity to further exploit electrogram signals as a means to determine catheter contact force.

SUMMARY OF THE INVENTION

The present invention is an automatic method of categorizing the contact force of a catheter tip against a portion of a patient's heart based on motion of the catheter tip. The method comprises: (a) capturing a series of 3D-coordinate data points of the catheter tip as a function of discrete times with a 3D medical imaging system, the 3D coordinates corresponding to an orthogonal 3-axis spatial coordinate system; (b) using a programmable computing system to compute a set of measures based on the series of 3D-coordinate data points; (c) categorizing each measure by a respective set of predetermined threshold values; and (d) combining the categorized measures to yield a relative quality of the contact force.

In highly-preferred embodiments of the automatic catheter-tip contact-force categorization method, the measures are first, second, and third measures, and the first measure is determined by computing a total-least-squares-fit plane for the series of 3D-coordinate data points and computing the average perpendicular distance to the plane for the points in the series. In some of these embodiments, the second measure is determined by (a) creating a set of 2D data points by perpendicularly projecting the 3D-coordinate data points onto the plane, (b) computing the major and minor axes lengths of the set of 2D data points, and (c) computing the ratio of the long-axis length to the short-axis length.

In some highly-preferred embodiments, the third measure is determined by: (1) selecting 1D-coordinate values from one of the three axes; (2) dividing the selected 1D-coordinate values into heartbeat-length sections; and (3) computing a similarity of the 1D-coordinate sections. In some of these embodiments, the one axis is the axis which is most closely orthogonal to the anterior/posterior and inferior/ superior axes of the patient, and some of these embodiments further include providing an R-wave detector and the step of selecting 1D-coordinate values from one of the three axes includes: (1) dividing the data points into heartbeat-length sections using times of detected R-waves; (2) computing a similarity of the heartbeat sections of the 1D-coordinate values of each of the three axes; and (3) selecting the set of 1D-coordinate values having the highest similarity.

In some highly-preferred embodiments, similarity is computed using dynamic time warping.

Some preferred embodiments include categorizing contact force by a predetermined set of contact-force threshold values, and in some of these embodiments, the contact-force categories include weak, medium, good, and strong. In some of these embodiments, contact force is f expressed in grams-force and its categories are: weak for f<5; medium for 5<f≤10; good for 10<f≤30; and strong for f>30.

In some preferred embodiments, the categories for the first measure are small, medium, and large; for the second measure, small, medium, and large; and for the third measure, similar and dissimilar. In some of these preferred embodiments, the first measure is $m_1$ expressed in millimeters and its categories are: small for $0<m_1≤0.25$; medium for $5<m_1≤0.5$; and large for $m_1>0.5$. In some preferred embodiments, the second measure is $m_2$ and its categories are: small for $0<m_2≤2$; medium for $2<m_2≤4$; and large for $m_2>4$. In some preferred embodiments, the third measure is computed using dynamic time warping and is $m_3$ expressed in millimeters squared ($mm^2$) and its categories are: similar for $0<m_3≤0.8$; and dissimilar for $m_3>0.8$.

Some highly-preferred embodiments of the automatic catheter-tip contact-force categorization method include combining the categorized measures using a multi-class classification decision tree.

In another aspect of the automatic method of categorizing the contact force of a catheter tip against a portion of a patient's heart based on motion of the catheter tip, the method comprises: (a) capturing a series of 3D-coordinate data points of the catheter tip as a function of time with a 3D medical imaging system, the 3D coordinates corresponding to a spatial coordinate system; (b) using a programmable computing system to generate a set of measures based on the series of 3D-coordinate data points; and (c) combining the measures to yield a relative quality of the contact force.

The term "3D medical imaging system" as used herein refers to any system, apparatus and/or devices from which the spatial coordinates of the location of a medical object such as a cardiac catheter, and in particular, the location of the tip of such catheter, are derived. Such systems, apparatus, and/or devices include but are not limited to systems such as (a) a fluoroscopic system using back-projection analysis, (b) a system deriving such coordinates from a single-plane fluoroscope such as the Navik 3D system from APN Health, LLC of Pewaukee, Wis. and described in U.S. Pat. No. 9,986,931 titled "Automatically Determining 3D Catheter Location and Orientation Using 2D Fluoroscopy Only", and (c) a system employing impedance measurements across a patient's chest. Other such systems, apparatus, and/or devices are also within the scope of the claims of the present invention.

The term "anterior/posterior axis" of a patient as used herein refers to an axis generally in the front-to-back direction of the patient.

The term "inferior/superior axis" of a patient as used herein refers to an axis generally in the head-to-foot direction of the patient.

Measure $m_1$ as described herein is expressed in millimeters. The use of millimeter distance units is not intended to be limiting to the scope of the present invention. Other distance units can be used, with a commensurate adjustment to the corresponding predetermined threshold values.

Measure $m_3$ as described herein is expressed in millimeters squared. The use of millimeters squared ($mm^2$) to express squared Euclidean distance is not intended to be limiting to the scope of the present invention. Other squared distance units can be used, with a commensurate adjustment to the corresponding predetermined threshold values.

BRIEF DESCRIPTION OF THE DRAWINGS

FIGS. 3A through 3C illustrate a set of 3D plots of an exemplary series of sequential 3D-coordinate data points of a catheter tip as a function of discrete times. The 3D coordinates are the values in an orthogonal 3-axis spatial coordinate system XYZ.

FIGS. 5A through 5C illustrate the same points as shown in FIGS. 3A-3C but with the addition of the total-least-squares-fit plane also being shown.

FIGS. 6A through 6C illustrate the total-least-squares-fit plane onto which each of the 69 points has been perpendicularly projected.

FIG. 10 presents a series of exemplary data sets for training a multi-class classification decision tree with two inputs each having three categories, one input having two categories, and an output having four categories.

FIG. 11 presents four exemplary test-data sets having been processed by the simplified example herein.

FIGS. 14A through 15B illustrate a pair of electrogram signals and their frequency distributions. FIG. 14A is the time-series plot of an exemplary ablation catheter-tip electrogram signal for which there is good contact (very high contact force CF) between the catheter tip and cardiac tissue, and FIG. 14B is the frequency distribution of the times series of FIG. 14A.

FIG. 15A is the time-series plot of an exemplary reference-electrode electrogram signal for which there is good contact between the reference electrode and cardiac tissue, and FIG. 15B is the frequency-distribution plot of the times series of FIG. 15A. The time-series data of FIGS. 14A and 15A were simultaneously captured.

FIGS. 17A through 18B illustrate a second pair of exemplary electrogram signals and their frequency distributions. FIG. 17A is the time-series plot of an exemplary ablation catheter-tip electrogram signal for which there is poor contact (very low contact force CF) between the catheter tip and cardiac tissue, and FIG. 17B is the frequency distribution of the times series of FIG. 17A.

FIG. 18A is the time-series plot of an exemplary reference-electrode electrogram signal for which there is good contact between the reference electrode and cardiac tissue, and FIG. 18B is the frequency-distribution plot of the times series of FIG. 18A. The time-series data of FIGS. 17A and 18A were simultaneously captured.

DETAILED DESCRIPTION OF PREFERRED EMBODIMENTS

Figure 1:
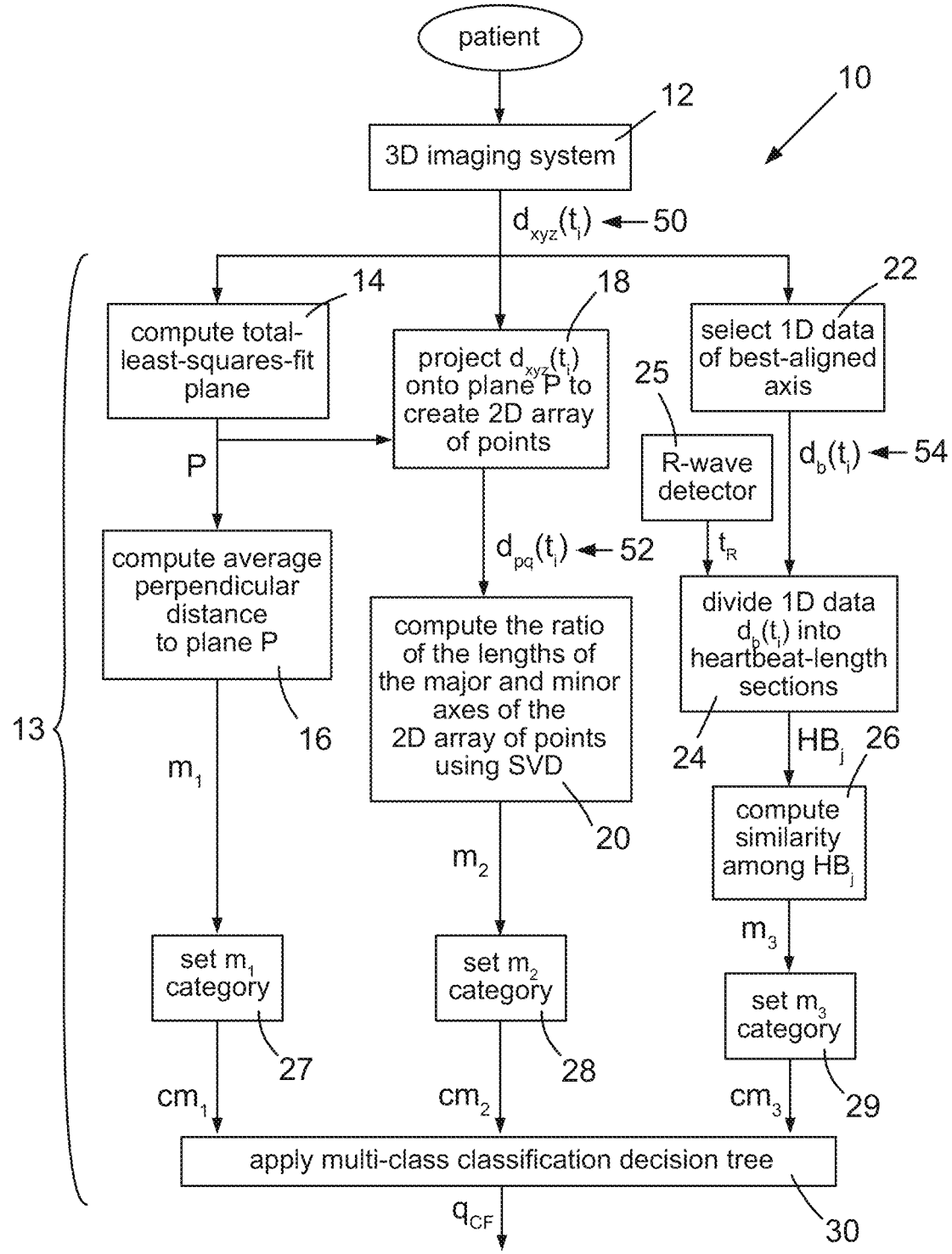
FIG. 1 is a schematic block diagram of an embodiment of the inventive automatic method of categorizing the contact force of a catheter tip against a portion of a patient's heart based on motion of the catheter tip.
Figure 2A:
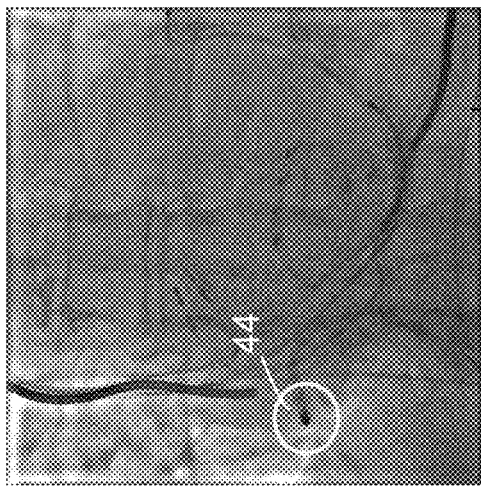
FIGS. 2A through 2F are a series of three exemplary two-dimensional (2D) fluoroscopic image pairs from which three-dimensional (3D) coordinates can be extracted using fluoroscopic image back-projection. Back-projection is one exemplary method by which 3D coordinates of medical objects can be captured.
Figure 2B:
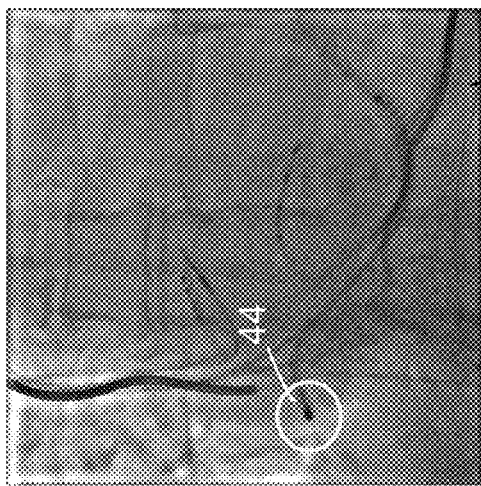
Figure 2C:
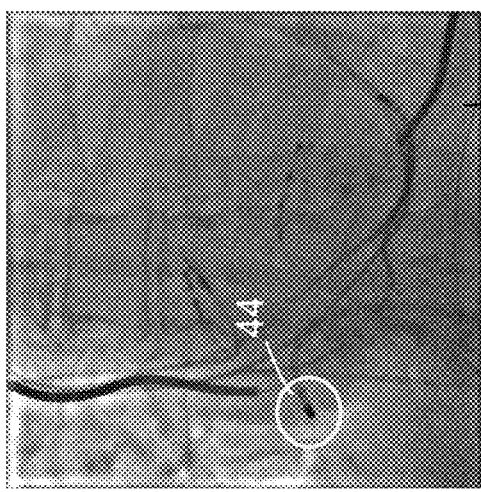
Figure 2D:
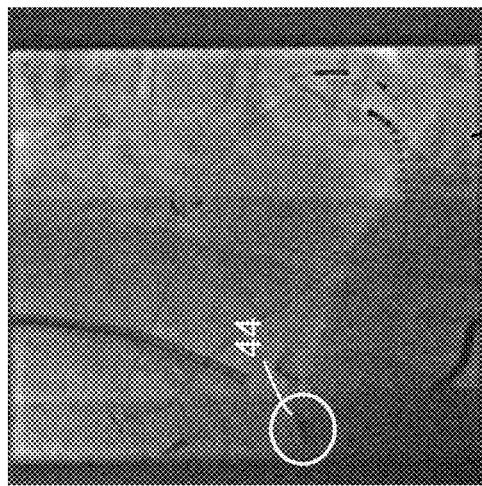
Figure 2E:
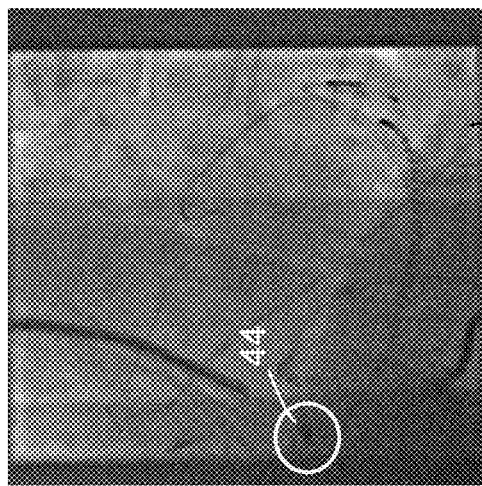
Figure 2F:
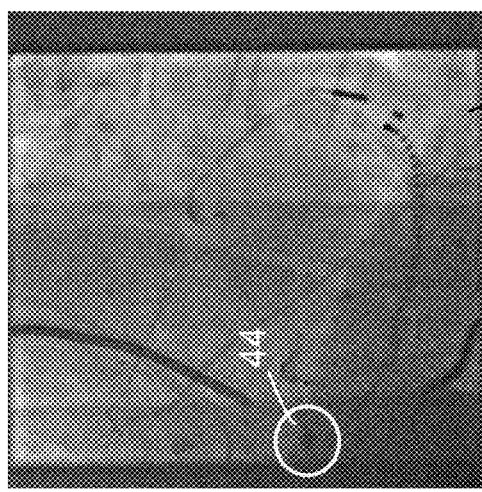

FIG. 1 is a schematic block diagram of an embodiment 10 of the inventive automatic method of categorizing the contact force CF of a catheter tip 44 (see FIGS. 2A-2F) against a portion of a patient's heart based on motion of catheter tip 44. A 3D medical imaging system 12 is used to capture data points $d_{xyz}(t_i)$ (also labeled with reference number 50). Data points 50 are a series of 3D-coordinate data points of catheter tip 44 as a function of discrete times $t_i$, from 3D medical imaging system 12, the 3D coordinates corresponding to an orthogonal 3-axis spatial coordinate system XYZ. In the example, the series of data points 50 is captured at the rate of 15 points per second (pps). Data points 50 are triplets of orthogonal spatial coordinate values expressed in millimeters (mm).

3D medical imaging system sequentially captures 2D fluoroscopic images from two different angles (biplane fluoroscopy) and uses back-projection analysis to determine the 3D coordinates of catheter tip 44. FIGS. 2A through 2F are a series of three pairs of exemplary 2D fluoroscopic images (32, 38), (34, 40), and (36, 42) from which 3D coordinates (data points 50) of catheter tip 44 have been extracted using fluoroscopic image back-projection. As described above, back-projection is one exemplary method by which 3D coordinates of medical objects can be captured.

The 2D image frames of FIGS. 2A-2C and 2D-2F are captured sequentially using biplane fluoroscopy, with images 32, 34, and 36 anterior/posterior (AP) views and images 38, 40, and 42 being the concurrent lateral anterior oblique (LAO) views. Using the 2D catheter-tip positions from each concurrent pair of frames and the geometry of the fluoroscopic system, the 3D coordinates of catheter tip 44 are determined using back-projection analysis. Such back-projection calculations are well-known to those skilled in the area of mathematics and need not be described further herein. Fluoroscopic images 32-42 were captured using a frame rate of 15 frames per second (fps), corresponding to a data rate of 15 pps. The use of such a data rate is not intended to be limiting; other data-capture rates, including but not limited to 7.5 pps and 3.75 pps, are within the scope of the present invention.

Referring now to FIG. 1, method embodiment 10 includes the use of a programmable computing system 13 which is indicated by an ellipsis, indicating that the various method steps or elements are carried out in an automatic fashion by programmable computing system 13. In method step 14, a total-least-squares-fit plane P of data points 50 is computed. For any such set of 3D data points 50, plane P is the unique linear plane which minimizes the sum of the perpendicular distances $D_p$ (see FIG. 5C) to plane P from every point in data points 50. Mathematical procedures such as singular-value decomposition (SVD) and principal component analysis (PCA) are able to process data points 50 to find plane P. Such procedures are well-known to those skilled in the area of linear algebra and need not be described further herein.

In method step 16, the average of perpendicular distances $D_p$ from data points 50 to plane P is computed, and is a first measure $m_1$ from which a quality $qc_{CF}$ of catheter contact force CF is determined. It has been recognized that if there is strong contact between catheter tip 44 and cardiac tissue, the primary factor affecting the motion of catheter tip 44 is myocardial contraction. If the contact between the cardiac tissue and catheter tip 44 is weak (lower contact force), other sources of motion, such as breathing or blood circulation, may dominate the motion of catheter tip 44. When myocardial contraction dominates motion of catheter tip 44, data points 50 are more likely to form a plane. Thus, there is a useful relationship between cardiac catheter force CF and the planar character of data points 50. This relationship is described by measure $m_1$, the average of perpendicular distances $D_p$ between plane P, which best represents the planar character of data points 50, and data points 50.

Figure 4:
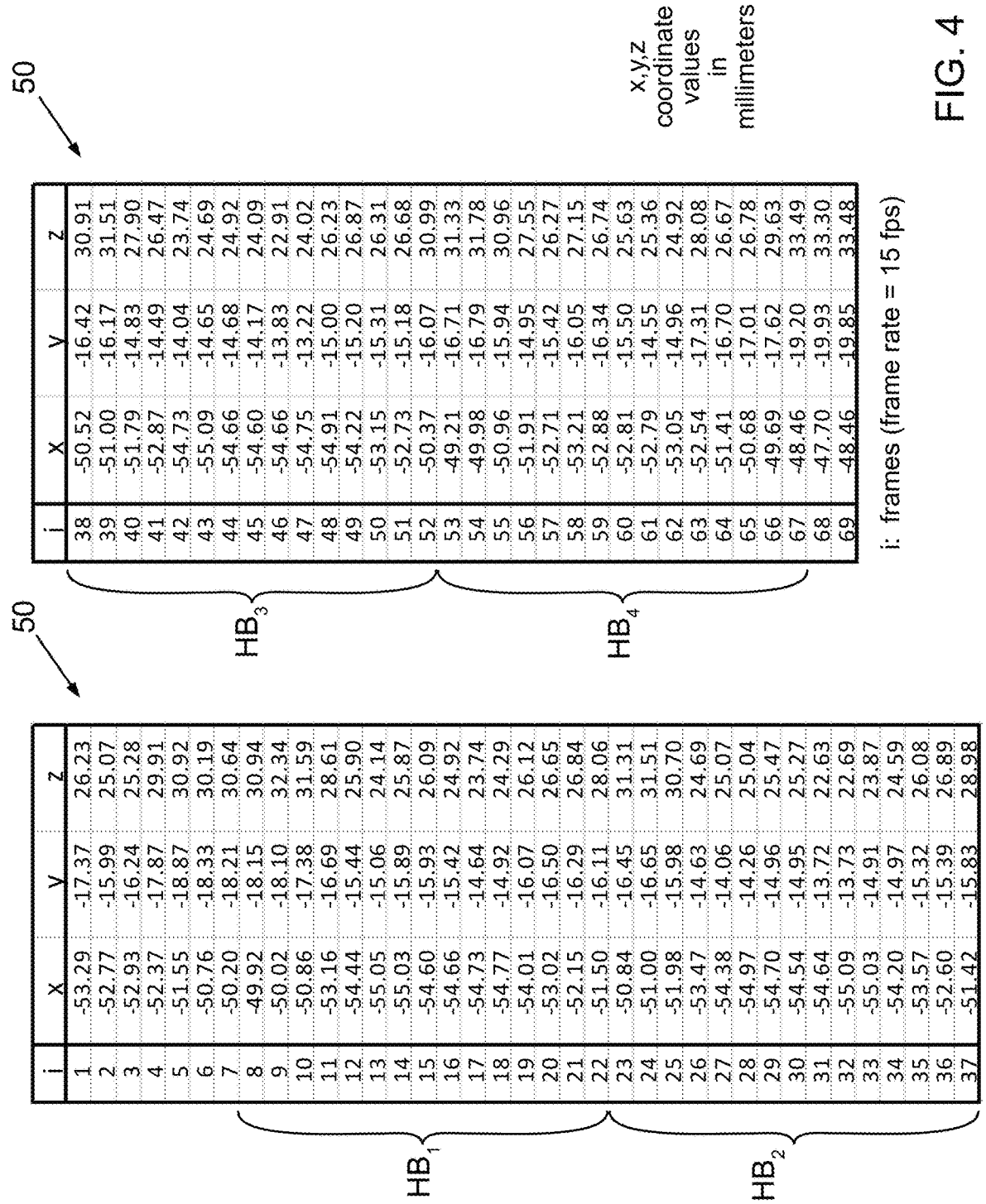
FIG. 4 is a table of the exemplary data points plotted in FIGS. 3A-3C and used throughout the example presented herein.

FIGS. 3A through 3C illustrate a set of 3D plots of an exemplary series of sequential 3D-coordinate data points 50 of catheter tip 44 as a function of discrete times $t_i$. (FIG. 4 is a table of 69 exemplary data points 50 plotted in FIGS. 3A-3C and used throughout the example presented herein.) The 3D coordinates are the values x,y,z in an orthogonal 3-axis spatial coordinate system XYZ as shown. FIGS. 3A-3C are presented with the XYZ axes in three different orientations simply to more easily appreciate the 3D character of data points 50.

Note that the 3D plots in FIGS. 3A-3C as well as in FIGS. 5A-5C and FIGS. 6A-6C are all presented in perspective views which render distances closer to the viewer as much larger than the equivalent distances further from the viewer.

FIGS. 5A through 5C illustrate data points 50 in similar fashion to FIGS. 3A-3C but with the addition of total-least-squares-fit plane P. As in FIGS. 3A-3C, FIGS. 5A-5C are presented in three different orientations. In FIG. 5B, plane P is tilted more toward the vertical (with respect to the page) than in FIG. 5A, and in particular, FIG. 5C is oriented such that total-least-squares-fit plane P is perpendicular to the plane of the page.

As indicated in FIGS. 5A-5B, the result of the SVD computation for data points 50 in method step 14 is that total-least-squares-fit plane P is represented by the linear equation z=2.11x+0.74y+150.47, and as indicated in FIG. 5C, the average of perpendicular distances $D_p$ to plane P for data points 50 as computed in method element 16 as $m_1$=0.48 mm.

Referring again to FIG. 1, in method step 18, data points 50 are each projected onto plane P to create a 2D array of points $d_{pq}(t_i)$ (also labeled with reference number 52). The subscript "pq" indicates that the coordinates of 2D array 52 are in general different from any two of x, y, and z. The plots of FIGS. 6A through 6C illustrate total-least-squares-fit plane P onto which each of the 69 points of data points 50 has been perpendicularly projected, and the points shown in FIGS. 6A-6C are the points of 2D array 52. As in FIG. 5C, plane P is presented perpendicular to the page to illustrate that points 52 are points in plane P.

Figure 7:
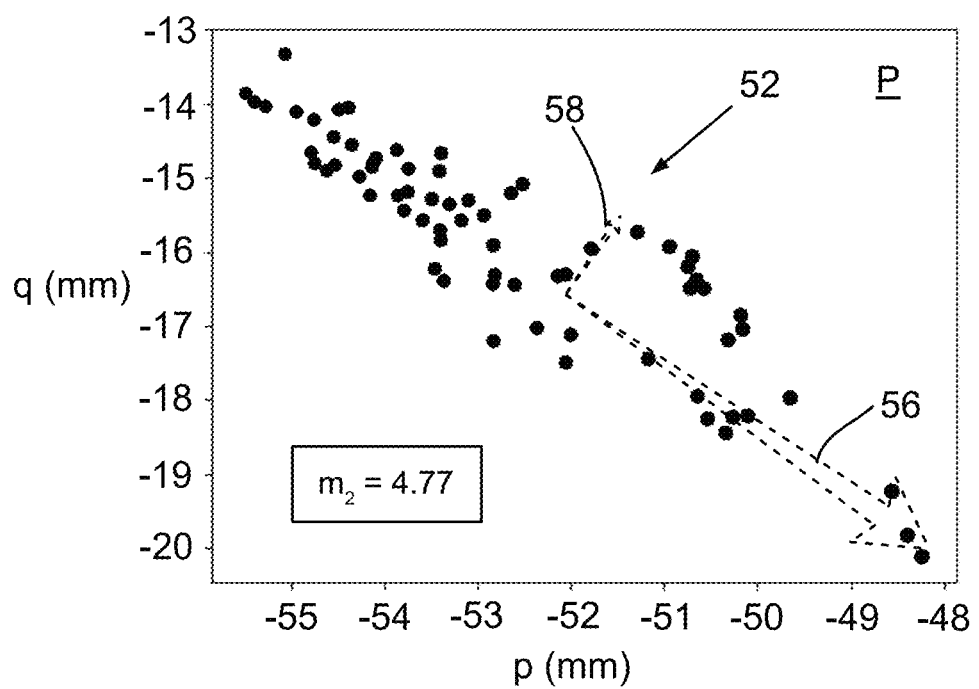
FIG. 7 is a 2D plot of the 69 points projected onto the total-least-squares-fit plane with such plane in the plane of the page.

A second measure $m_2$ of the quality of catheter contact force CF is computed in method step 20. FIG. 7 is a 2D plot of array 52. The plot of FIG. 7 presents plane P in the plane of the page, illustrating the extent of array 52. Measure $m_2$ is the ratio of the major axis 56 to the minor axis 58, which in the example is indicated as 4.77. In embodiment 10, the determination of major axis 56 and minor axis 58 is done again using SVD. The dotted-line arrows representing major axis 56 and minor axis 58 are not shown to scale as lengths determined by the SVD procedure (due to unit changes within the procedure), but the ratio of such lengths is represented properly in FIG. 7. Other approaches to determining the ratio of measure $m_2$, such as PCA, may be used; the use of SVD in embodiment 10 is not intended to be limiting.

The shape of 2D array 52, as represented by measure $m_2$, also relates to contact force CF with the cardiac tissue. As mentioned above, when catheter contact force CF is strong, the motion of catheter tip 44 is dominated by the myocardial contraction of the heart. The movement in myocardial contraction is largely a back-and-forth motion, thus, when catheter contact force is strong, the motion of catheter tip 44 is more linear than when contact force CF is weak. The reduced linear motion is likely influenced by flow of the surrounding blood which causes deviation from linear movement, spreading out the path of catheter tip 44. Thus, as above with measure $m_1$, there is a helpful relationship between cardiac catheter force CF and the spread of 2D array 52. This relationship is described by measure $m_2$, the ratio of the major and minor axes of 2D array 52 which represents the spread of the points in 2D array 52.

Figure 8A:
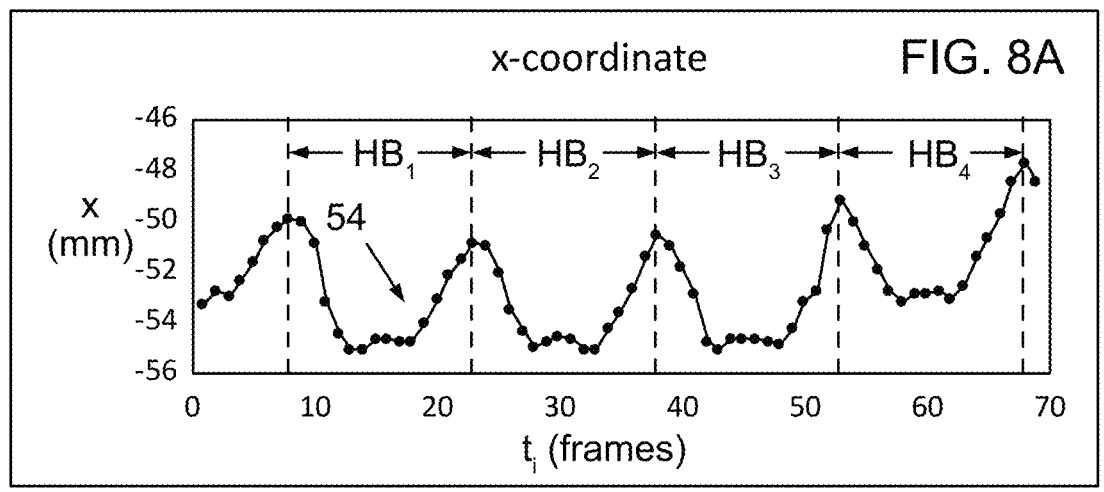
FIG. 8A through 8C are discrete-time plots of the x, y, and z coordinates, respectively, of the 69 data points of the example (see FIG. 4).
Figure 8B:
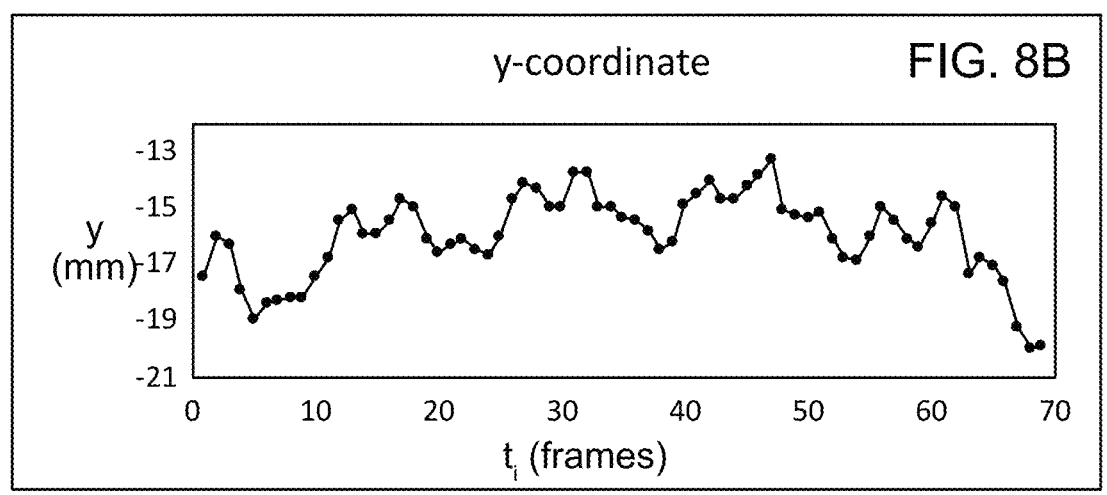
Figure 8C:
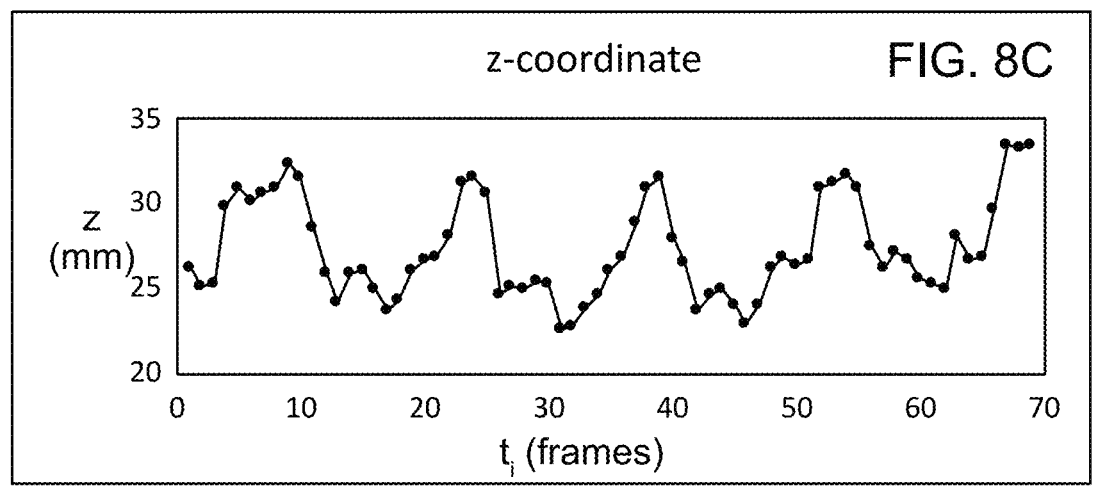
Figure 9A:
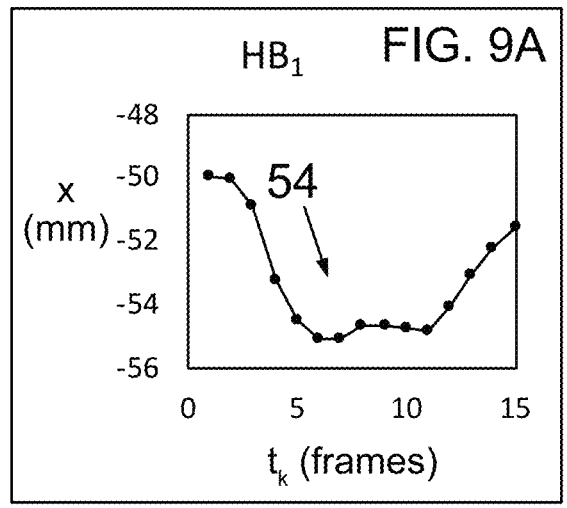
FIGS. 9A through 9D are four discrete-time plots of the x-coordinate data within four of the heartbeats shown in FIG. 8A and also seen in FIG. 4. The heartbeats are labeled $HB_1$, $HB_2$, $HB_3$, and $HB_4$, respectively.
Figure 9B:
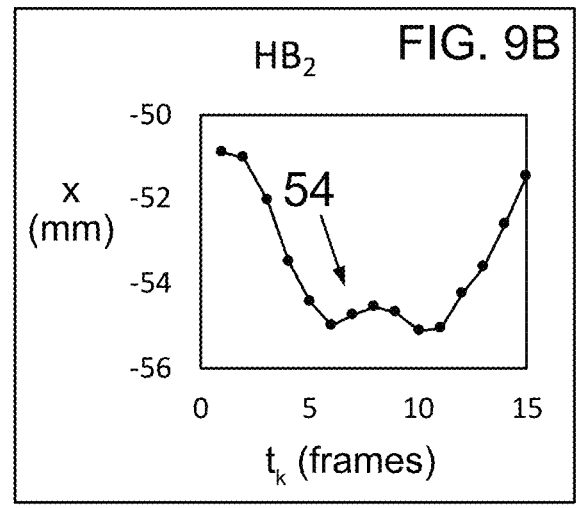
Figure 9C:
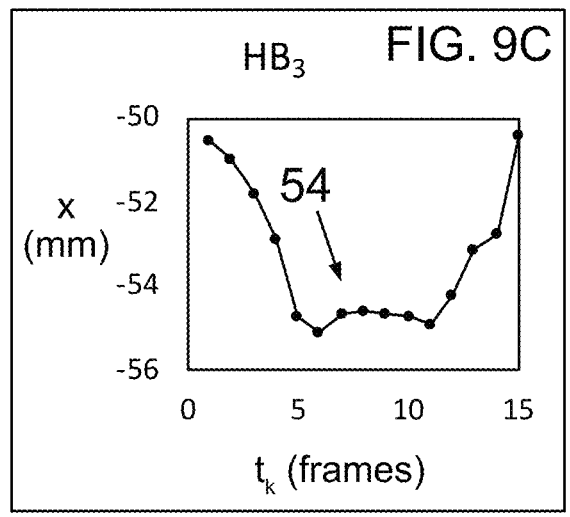
Figure 9D:
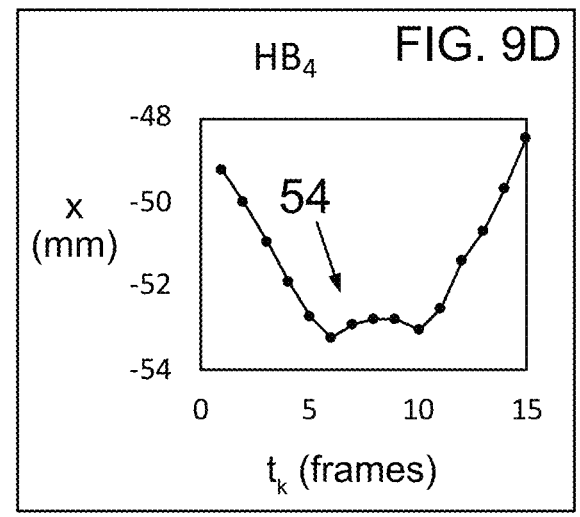

In addition to being analyzed spatially as a 3D array of points as in determination of measure $m_1$ and as projections onto 2D plane P as in the determination of measure $m_2$, the time-dependent character of data points 50 can also be assessed. It has been found that the stability of catheter/tissue contact (and thus contact force CF) is related to the similarity among multiple heartbeats of the dynamic behavior of one or more of the three 1D coordinates in data points 50. Each set of 1D coordinates in data points 50 is a short time series of values. (FIGS. 8A through 8C illustrate the x, y, and z 1D-coordinate time series, respectively, for the example herein.)

Similarity among multiple heartbeats may be determined in a variety of ways, but one very useful way is to apply dynamic time warping (DTW) to compute a cost which is related to the shape similarity among multiple heartbeats. (A lower cost represents a higher degree of similarity.) DTW is well-known to those skilled in the area of time-series analysis and need not be further described herein.

Referring again to method embodiment 10 of FIG. 1, in method step 22, the 1D-coordinate values $d_b(t_i)$ (also labeled with reference number 54) of the best-aligned axis among data points 50 is selected. In embodiment 10, the term "best-aligned" refers to selecting the axis of the 3-axis coordinate system XYZ which is which is most closely orthogonal to the anterior/posterior and inferior/superior axes of the patient. In the example, the best-aligned axis is the x axis, preset based on the position of the patient during the setup of the medical procedure. Thus, 1D coordinates 54 are the x-coordinate values of data points 50.

Selection of the 1D coordinates may also be done using data points 50 in real time, by computing the similarity of each of the three 1D-coordinate sets in data points 50 and choosing 1D coordinates 54 having the highest similarity (lower cost as analyzed by DTW). (See FIGS. 8A through 8C for the three time series in the example.)

As illustrated in FIG. 1, in method step 24, 1D coordinates 54 are divided into heartbeat-length sections $HB_j$. In the example, there are four heartbeats in data points 50, as indicated in FIGS. 4 and 8A; thus j=1, 2, 3, 4 in the example.

Dividing 1D coordinates 54 into heartbeat-length sections in method step 24 can be done in several different ways. One approach, as illustrated in embodiment 10, involves providing an R-wave detector 25 from which times $t_R$ of R-wave occurrence indicate heartbeat phase which is then used to divide 1D coordinates 54 into heartbeat-length sections $HB_j$. A second approach involves dividing the 1D coordinates 54 into heartbeat-length sections $HB_j$ between local maxima of the selected-axis 1D coordinates. (Note that sections $HB_1$ through $HB_4$ as shown in FIG. 8A have been created using this second approach.)

FIGS. 9A-9D are plots of heartbeat sections $HB_1$-$HB_4$, respectively, each plot showing a section of 1D coordinates 54 (x-components of data points 50). In method step 26, similarity is calculated using DTW to compare $HB_1$ with $HB_2$, $HB_1$ with $HB_3$, and $HB_1$ with $HB_4$. Other comparison pairs are possible within the scope of this invention. In the example, the result of such calculation is $m_3$=0.69 mm$^2$ as shown with FIGS. 9A-9D. (Note that $m_3$ is expressed as squared Euclidean distance in mm$^2$.)

Catheter contact force CF is usefully categorized into four ranges, herein designated as weak, medium, good, and strong. Based on the experience of cardiologists, when contact force CF is characterized as "weak," it is insufficient for the medical procedure (typically cardiac ablation) being undertaken and needs to be increased by the physician. Contact force CF characterized as "medium" means that contact force CF (catheter tip/tissue contact) is adequate but less than desirable. Contact force CF characterized as "good" is at the most desirable level for the procedure, and if contact force CF is characterized as strong, there may be a risk of perforating the tissue or other adverse effects.

These four levels, weak, medium, good, and strong, describe the quality of contact force CF. Such quality levels are sufficiently descriptive of catheter-tip/tissue contact to be of great use during cardiac procedures such as cardiac ablation. One useful set of threshold values expressed in grams-force by which to categorize contact force has been found to be weak (0<5), medium (5<CF≤10), good (10<CF≤30), and strong (>30). The number, nomenclature, and specific thresholds for such categories are not intended to be limiting to the scope of the present invention.

It has also been found that it is useful to categorize measures $m_1$, $m_2$, and $m_3$ in a fashion similar to that of contact force CF. One set of useful categories for categorizing measures $m_1$, $m_2$, and $m_3$ are as follows. The categories for the measure $m_1$ are small, medium, and large; for measure $m_2$, small, medium, and large; and for measure $m_3$, similar and dissimilar. A useful set of predetermined thresholds has been found to be as follows: $m_1$ (in mm)—small ($0 < m_1 \leq 0.25$), medium ($5 < m_1 \leq 0.5$), and large ($>0.5$); $m_2$—small ($0 < m_2 \leq 2$), medium ($2 < m_2 \leq 4$), and large ($>4$); and $m_3$ (in mm$^2$)—similar ($0 < m_3 \leq 0.8$) and dissimilar ($>0.8$).

Referring again to FIG. 1, in method steps 27, 28, and 29, measures $m_1$, $m_2$, and $m_3$ are assigned their respective categories $cm_1$, $cm_2$, and $cm_3$, and in method step 30, these categorized measures $cm_1$, $cm_2$, and $cm_3$ are combined by being inputs to a previously-trained multi-class classification decision tree. Multi-class classification decision trees are well-known to those skilled in the area of machine learning and therefore need not be described in detail herein.

The training of multi-class classification decision trees uses sets of data which include data sets having a categorized value for each measure (i.e., $cm_1$, $cm_2$, and $cm_3$ and a categorized value of CF, referred to in FIG. 1 as $q_{CF}$, where $q_{CF}$ is equal to one of the four categories describing contact force CF, i.e., strong, good, medium, and weak. Data sets for such training are generated using a system which is capable of measuring contact force CF while generating values for measures $m_1$, $m_2$, and $m_3$, for example, a system like that of embodiment 10 but with the addition of a specialized contact-force-measuring catheter.

FIG. 10 presents a series of exemplary data sets for training a multi-class classification decision tree with two inputs each having three categories, one input having two categories, and an output having four categories. FIG. 11 presents four exemplary test-data sets. The test case which is highlighted with an ellipse corresponds to the categories $cm_1$, $cm_2$, and $cm_3$ of the example described herein, and indicates in this simple case that contact force CF would have been categorized as having "good" quality.

A previously-trained multi-class classification decision tree has the property that given that training is complete, it operates essentially in a fashion like a look-up table; thus, a look-up table can be constructed from such a trained multi-class classification decision tree to streamline the function of combining of measures $m_1$, $m_2$, and $m_3$ in method step 30.

In a further aspect of automatically determining the contact force of a catheter tip against a portion of a patient's heart, since the electrical coupling between an electrode and tissue is related to the quality of the corresponding physical contact, a comparison of the stability of an electrogram signal from an ablation-catheter tip 62 with a known stable signal from another electrode (a reference electrode 66) can provide useful information.

Figure 12:
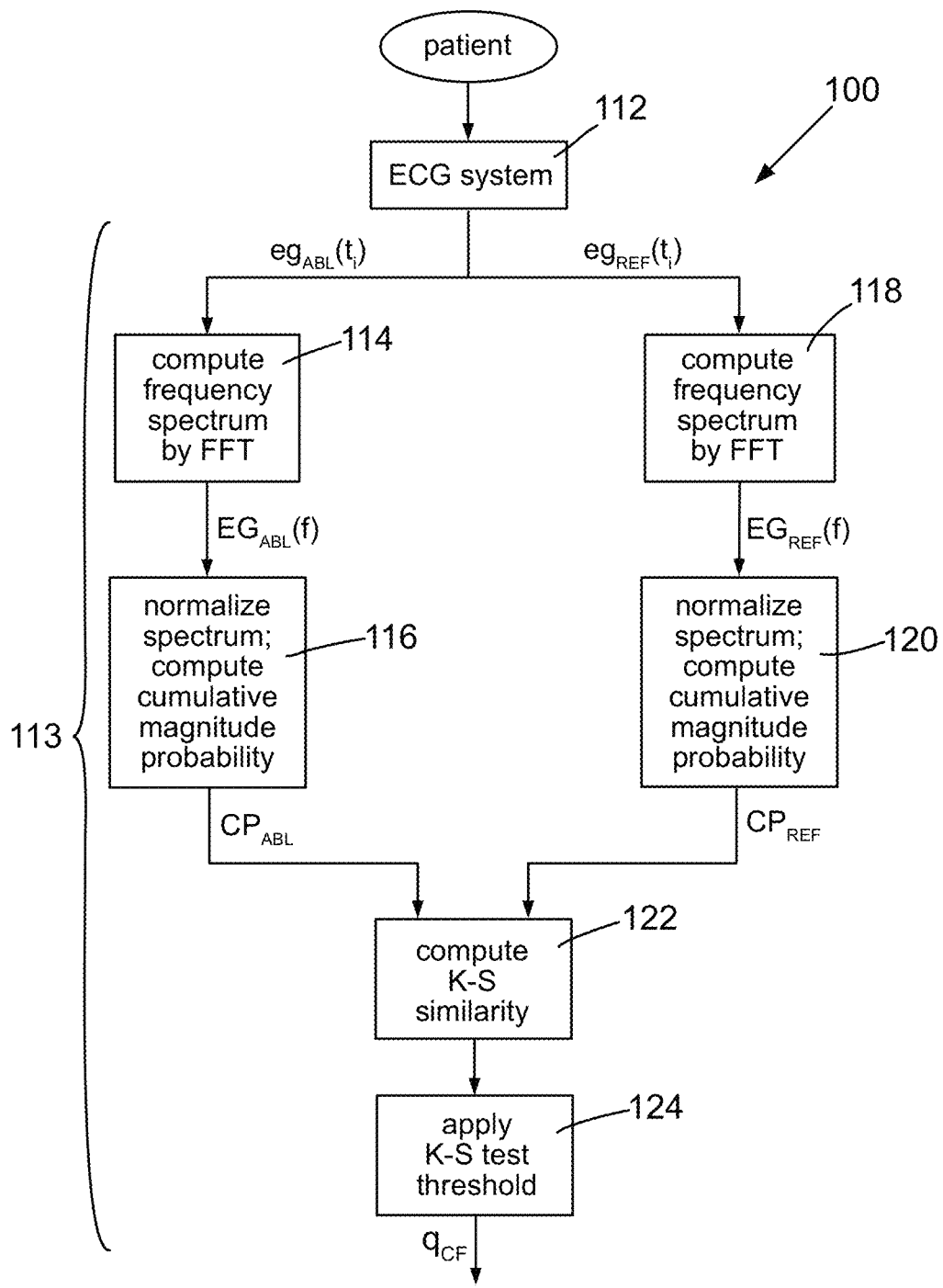
FIG. 12 is a schematic block diagram of an embodiment of an automatic method of categorizing the contact force of a catheter tip against a portion of a patient's heart based on the frequency content of electrogram signals.
Figure 13:
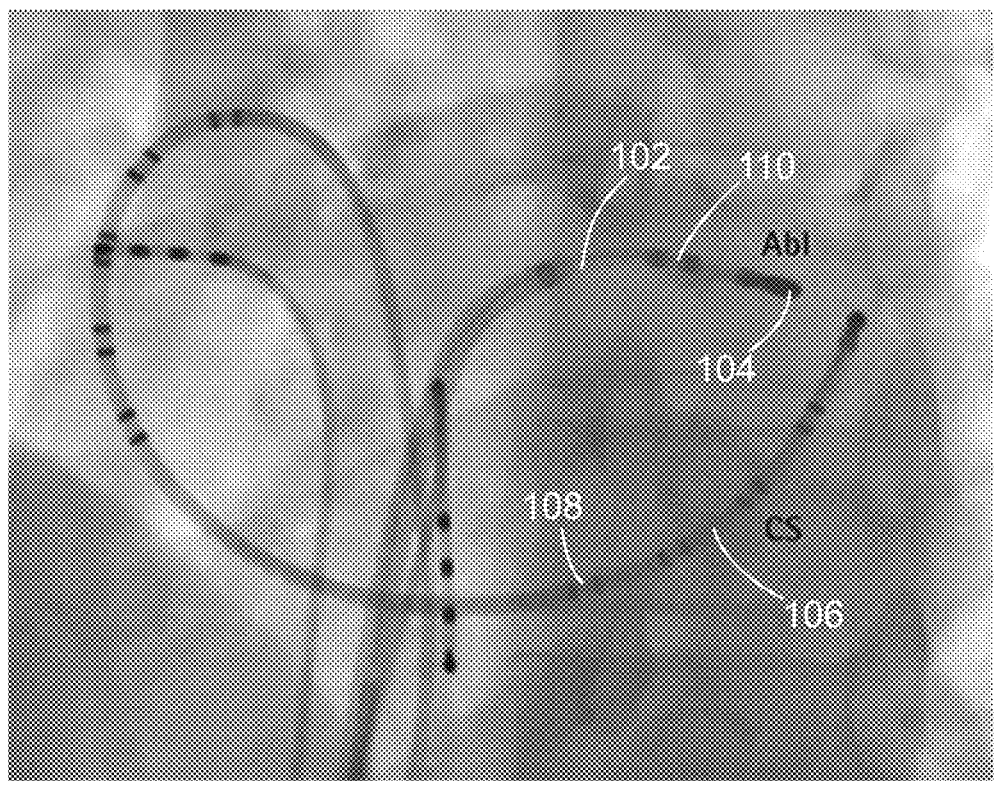
FIG. 13 is an exemplary fluoroscopic image illustrating an ablation catheter with an ablation-catheter tip and a coronary sinus catheter with a reference electrode, used for electrogram comparison.

FIG. 12 is a schematic block diagram of an embodiment 100 of an automatic method of categorizing catheter-tip contact force CF against a portion of a patient's heart based on the frequency content of electrogram signals from the heart. FIG. 13 is an exemplary fluoroscopic image illustrating an ablation catheter 102 (also labeled Abl) with ablation-catheter tip 104 and a coronary sinus (also labeled CS) catheter 106 with a reference electrode 108. Electrogram signals are captured from ablation-catheter tip 104 and reference electrode 108, which in this example is a proximal electrode 108 of coronary sinus catheter 106. In the example, CS electrode 108 is the $CS_{9-10}$ bipolar pair of electrodes. (Note that herein a bipolar pair of electrodes such as the $CS_{9-10}$ bipolar pair is also referred to as a single electrode since a single signal is derived therefrom.) FIG. 13 also illustrates an ablation-catheter proximal electrode 110 (bipolar pair 3-4).

The coronary sinus lies between the left atrium and left ventricle on the posterior side of the heart. When a catheter is placed in this location, activation of both the left atrium and the left ventricle can be sensed. Typically, the CS catheter sticks to the wall of the coronary sinus tightly, resulting in electrogram signals captured from CS catheter electrodes being very stable. The use of an electrogram signal from the coronary sinus catheter as a reference signal is not intended to be limiting; other stable electrogram signals may be used to compare with the signal from the catheter for which contact force CF is being determined. However, in the description of the example presented in FIGS. 13 through 20, the reference signal is indicated as being captured from a CS catheter.

Referring again to method embodiment 100 in FIG. 12, in method step 112, an electrogram signal $eg_{ABL}(t_i)$ of an electrode at ablation catheter tip 104 on ablation catheter 102 and an electrogram signal $eg_{CS}(t_i)$ of a reference electrode 108 on CS catheter 106 are captured. In method step 114, a frequency distribution EG(f) is computed. Such computation may be carried out using a fast Fourier transform (FFT) as indicated in embodiment 100, but other procedures for determining frequency (f) distribution EG(f) may be used; the use of an FFT is not intended to be limiting to the scope of the invention.

In method step 116, $EG_{ABL}(f)$ is normalized and a cumulative probability $CP_{ABL}$ of the magnitude of the normalized spectrum is computed. The process of computing frequency spectra, including by a FFT, is well-known to those skilled in the area of signal processing and need not be further described herein. In similar fashion, the process of computing cumulative probabilities of variables is well-known to those skilled in the area of statistics.

Method embodiment 100 includes the use of a programmable computing system 113 which is indicated by an ellipsis in FIG. 12, indicating that the various method steps or elements are carried out in an automatic fashion by programmable computing system 113.

In similar fashions, method steps 118 and 120 carry out the same computations as those of method steps 114 and 116, respectively, on reference electrogram signal $eg_{CS}(t_i)$ and frequency spectrum $EG_{CS}(f)$. The frequency spectra $EG_{ABL}(f)$ and $EG_{CS}(f)$ are normalized to have equivalent areas under the spectral curves prior to comparison in method step 122.

FIGS. 14A through 15B (designated as case 1) illustrate a pair of electrogram signals $eg_{ABL1}(t_i)$ and $eg_{CS1}(t_i)$ and their frequency distributions $EG_{ABL1}(f)$ and $EG_{CS1}(f)$. FIG. 14A is the time-series plot of an exemplary ablation catheter-tip electrogram signal $eg_{ABL1}(t_i)$ for which there is good contact (very high contact force CF [27 grams-force]) between catheter tip 104 and cardiac tissue, and FIG. 14B is the frequency distribution $EG_{ABL1}(f)$ of $eg_{SBL1}(t_i)$.

FIG. 15A is the time-series plot of reference-electrode 108 electrogram signal $eg_{CS1}(t_i)$ for which there is good contact between reference electrode 108 and cardiac tissue, and FIG. 15B is a plot of frequency-distribution $EG_{CS1}(f)$ of $eg_{CS1}(t_i)$. The time-series data of FIGS. 14A and 15A were simultaneously captured. Note that in all of the time-series plots herein (FIGS. 14A, 15A, 16, 17A, and 18A), the abscissa of such plots represents the time stamp values of the samples plotted, not every sample at times $t_i$ used in the frequency spectra computations. About 1000 samples were plotted in each such case. The length of each time series is several seconds, and electrogram data were captured at the rate of 1000 sps. Thus, the frequency range of the frequency spectra created by an FFT computation is 0 to 500 Hz, as shown.

Figure 16:
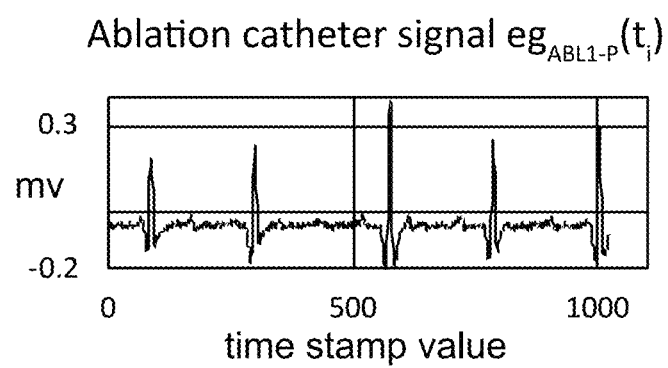
FIG. 16 is the time-series plot of an exemplary ablation catheter proximal-electrode electrogram signal captured simultaneously with the times series on FIGS. 14A and 15A.

FIG. 16 is the time-series plot of an exemplary ablation catheter proximal-electrode electrogram signal $eg_{ABLI-P}(t_i)$ captured simultaneously with the time series $eg_{ABLI}(t_i)$ and $eg_{CSI}(t_i)$. Time series $eg_{ABLI-p}(t_i)$ may be useful in assessing the orientation of ablation catheter 102.

FIG. 17A is the time-series plot of a second exemplary ablation catheter-tip electrogram signal $eg_{ABL2}(t_i)$ for which there is poor contact (very low contact force CF [1 gram-force]) between catheter tip 104 and cardiac tissue, and FIG. 17B is the frequency distribution $EG_{ABL2}(f)$ of $eg_{ABL2}(t_i)$.

FIG. 18A is the time-series plot of reference-electrode 108 electrogram signal $eg_{cs2}(t_i)$ for which there is good contact between reference electrode 108 and cardiac tissue, and FIG. 15B is a plot of frequency-distribution $EG_{cs2}(f)$ of $eg_{cs2}(t_i)$. The time-series data of FIGS. 14A and 15A were simultaneously captured. The data in FIGS. 17A through 18B are designated as case 2.

Referring again to FIG. 12, in method step 122 of method embodiment 100, comparison is made between the cumulative probability $CP_{ABL}$ and cumulative probability $CP_{REF}$ in order to determine a similarity between spectra $EG_{ABL}(f)$ and $EG_{REF}(f)$. Low values of similarity between spectra $EG_{ABL}(f)$ and $EG_{REF}(f)$ is indicative of poor contact between ablation catheter tip 104 and cardiac tissue as long as the contact of reference electrode 108 is good. And the opposite is also true—high values of similarity between spectra $EG_{ABL}(f)$ and $EG_{REF}(f)$ is indicative of good contact between ablation catheter tip 104 and cardiac tissue as long as the contact of reference electrode 108 is good.

There are a number of ways to determine the similarity of two frequency spectra, and one useful way is a Kolmogorov-Smirnov test (K-S test), which quantifies a distance between an empirical distribution function of a sample and the cumulative distribution function of a reference distribution, or between the empirical distribution functions of two samples. The two-sample K-S test is one of the most useful and general non-parametric methods for comparing two samples, since it is sensitive to differences in both location and shape of the empirical cumulative distribution functions of the two samples.

Figure 19:
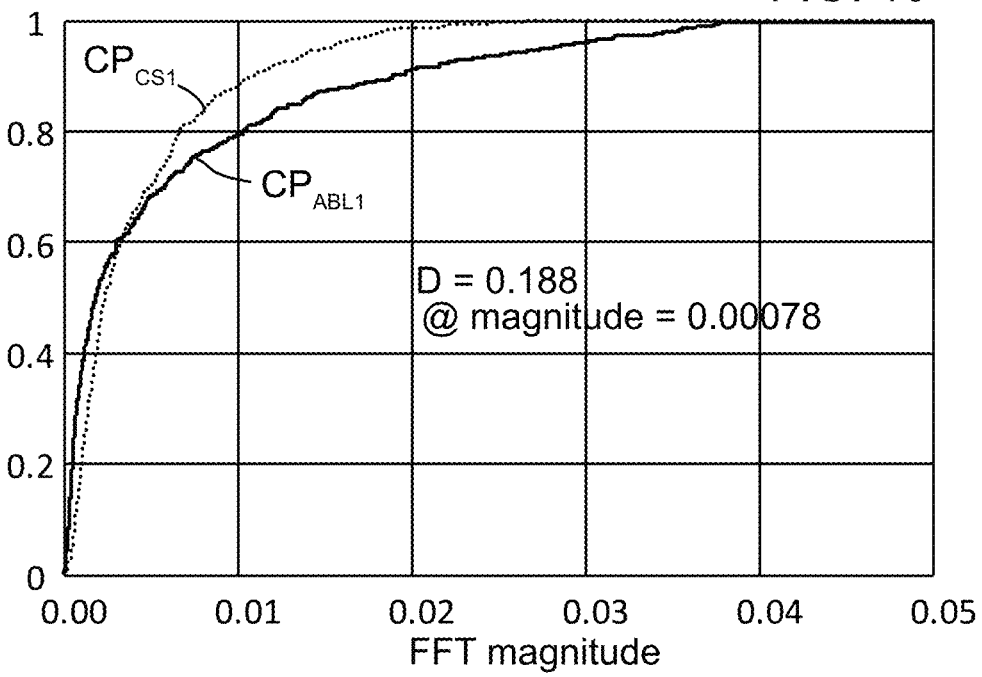
FIG. 19 presents plots of the cumulative probabilities of the FFT magnitudes of the frequency distributions of both FIGS. 14B (exemplary ablation catheter tip electrogram signal with the tip having good contact) and 15B (exemplary CS catheter reference electrogram signal).
Figure 20:
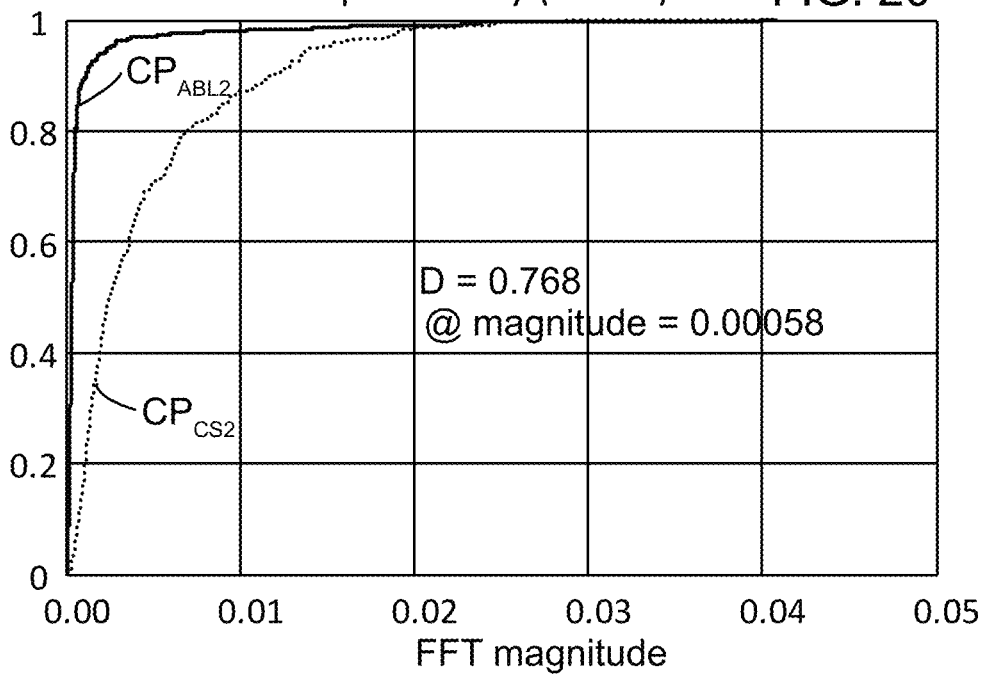
FIG. 20 presents plots of the cumulative probabilities of the normalized FFT magnitudes of the frequency distributions of both FIGS. 17B (exemplary ablation catheter tip electrogram signal with the tip having poor contact) and 18B (exemplary CS catheter reference electrogram signal).

FIGS. 19 and 20 illustrate the results of applying a K-S test for the two cases in the example herein using the FFT magnitude and the variable of interest. FIG. 19 (case 1) presents plots of the cumulative probabilities of the magnitudes of the frequency distributions of both FIGS. 14B (exemplary ablation catheter tip electrogram signal with the tip having good contact) and 15B (exemplary CS catheter reference electrogram signal).

FIG. 20 (case 2) presents plots of the cumulative probabilities of the magnitudes of the frequency distributions of both FIGS. 17B (exemplary ablation catheter tip electrogram signal with the tip having poor contact) and 18B (exemplary CS catheter reference electrogram signal).

In these examples, a single measure (difference D) is used to determine similarity between the two spectra. D is the maximum distance between the two cumulative probabilities, as illustrated in FIGS. 19 and 20. In FIG. 19, in which contact force CF is very high, the value of D is 0.188, which occurs at FFT magnitude=0.00078. In FIG. 20, in which contact force CF is very low, the value of D is 0.768, which occurs at FFT magnitude=0.00058. Note that lower values of D indicate higher values of similarity.

In method step 124, a predetermined threshold value for measure D, or multiple threshold values, which have been experimentally determined, are applied, thereby categorizing contact force by a quality value $q_{CF}$.

Note that FFT magnitude is not the only characteristic of frequency spectra which can be used. The use of FFT magnitude is not intended to be limited; other characteristics may be used to assess spectral similarity.

While the principles of this invention have been described in connection with specific embodiments, it should be understood clearly that these descriptions are made only by way of example and are not intended to limit the scope of the invention.

The invention claimed is:

1. An automatic method of categorizing the contact force of a catheter tip against a portion of a patient's heart based on motion of the catheter tip, the method comprising:
    capturing a series of 3D-coordinate data points of the catheter tip as a function of discrete times with a 3D medical imaging system, the 3D coordinates corresponding to an orthogonal 3-axis spatial coordinate system;
    computing first, second, and third measures based on the series of 3D-coordinate data points using a programmable computing system, the first measure being determined by computing a total-least-squares-fit plane for the series of 3D-coordinate data points and computing the average perpendicular distance to the plane for the points in the series;
    categorizing each measure by a respective set of predetermined threshold values; and
    combining the categorized measures to yield a relative quality of the contact force.

2. The automatic catheter-tip contact-force categorization method of claim 1 wherein the second measure is determined by (a) creating a set of 2D data points by perpendicularly projecting the 3D-coordinate data points onto the plane, (b) computing the major and minor axes lengths of the set of 2D data points, and (c) computing the ratio of the long-axis length to the short-axis length.

3. The automatic catheter-tip contact-force categorization method of claim 2 wherein the third measure is determined by:
    selecting 1D-coordinate values from one of the three axes;
    dividing the selected 1D-coordinate values into heartbeat-length sections; and
    computing a similarity of the 1D-coordinate sections.

4. The automatic catheter-tip contact-force categorization method of claim 3 wherein the one axis is the axis which is most closely orthogonal to the anterior/posterior and inferior/superior axes of the patient.

5. The automatic catheter-tip contact-force categorization method of claim 3 further including providing an R-wave detector and wherein selecting 1D-coordinate values from one of the three axes includes:
    dividing the data points into heartbeat-length sections using times of detected R-waves;
    computing a similarity of the heartbeat sections of the 1D-coordinate values of each of the three axes; and
    selecting the set of 1D-coordinate values having the highest similarity.

6. The automatic catheter-tip contact-force categorization method of claim 3 wherein similarity is computed using dynamic time warping.

7. The catheter-tip contact-force categorization method of claim 3 further including categorizing contact force by a predetermined set of contact-force threshold values.

8. The automatic catheter-tip contact-force categorization method of claim 7 wherein the contact-force categories include weak, medium, good, and strong.

9. The automatic catheter-tip contact-force categorization method of claim 8 wherein contact force is f expressed in grams-force and its categories are:
weak for f<5;
medium for 5<f≤10;
good for 10<f≤30; and
strong for f >30.

10. The automatic catheter-tip contact-force categorization method of claim 8 wherein:
the categories of the first measure include small, medium, and large;
the categories of the second measure include small, medium, and large; and
the categories of the third measure include similar and dissimilar.

11. The automatic catheter-tip contact-force categorization method of claim 10 wherein the first measure is $m_1$ expressed in millimeters and its categories are:
small for $0<m_1≤0.25$;
medium for $5<m_1≤0.5$; and
large for $m_1>0.5$.

12. The automatic catheter-tip contact-force categorization method of claim 10 wherein the second measure is $m_2$ and its categories are:
small for $0<m_2≤2$;
medium for $2<m_2≤4$; and
large for $m_2 >4$.

13. The automatic catheter-tip contact-force categorization method of claim 10 wherein similarity is computed using dynamic time warping, the third measure is $m_3$ expressed in millimeters squared and its categories are:
similar for $0<m_3≤0.8$; and
dissimilar for $m_3>0.8$.

14. The automatic catheter-tip contact-force categorization method of claim 10 wherein combining the categorized measures includes using a previously-trained multi-class classification decision tree.

15. The automatic catheter-tip contact-force categorization method of claim 8 wherein combining the categorized measures includes using a previously-trained multi-class classification decision tree.

* * * * *